United States Patent [19]
Farcasiu et al.

[11] Patent Number: 6,143,939
[45] Date of Patent: Nov. 7, 2000

[54] METHOD OF DEHALOGENATION USING DIAMONDS

[75] Inventors: Malvina Farcasiu, Roslyn Harbor, N.Y.; Phillip B. Kaufman, Lafayette, La.; Edward P. Ladner, Pittsburgh; Richard R. Anderson, Brownsville, both of Pa.

[73] Assignee: The United States of America as represented by the United States Department of Energy, Washington, D.C.

[21] Appl. No.: 09/259,419

[22] Filed: Feb. 26, 1999

[51] Int. Cl.[7] ............................. C07C 17/25; C07C 1/00
[52] U.S. Cl. ............................. 570/227; 585/641
[58] Field of Search ............................. 570/227; 585/641

[56] References Cited

PUBLICATIONS

M. Farcasiu, J.G. Lavin, P.B. Kaufamn, S. Subramoney, N.F. Bailey "Catalysis by Diamonds and other forms of carbons" Abstract and Presentation at 211th ACS Meeting, New Orleans, Mar. 24–29, 1996.

"Diamonds in Detonatin Soot" *Nature* 333 pp. 440–442 (Jun. 2, 1988) Authors: N. Roy Greiner, D.S. Phillips, J.D. Johnson and Fred Volk.

"Synthesis of Ultradispersed Diamond in Detonation Waves" *Combustion, Explosion and Shock Waves* 25 No. 3, pp. 372–379. Authors: V.M. Titov et al. (1989).

"Influence of the Molecular Structure of Explosives on the Rate of Formation, Yield, and Properties of Ultradisperse Diamond" *Combustion, Explosion and Shock Waves* 30 No. 2, pp. 235–238. Authors: S.V. Pershin et al. (1994).

*Primary Examiner*—Alan Siegel
*Attorney, Agent, or Firm*—Mark P. Dvorscak; Mark F. LaMarre; William R. Moser

[57] ABSTRACT

A method for preparing olefins and halogenated olefins is provided comprising contacting halogenated compounds with diamonds for a sufficient time and at a sufficient temperature to convert the halogenated compounds to olefins and halogenated olefins via elimination reactions.

16 Claims, 1 Drawing Sheet

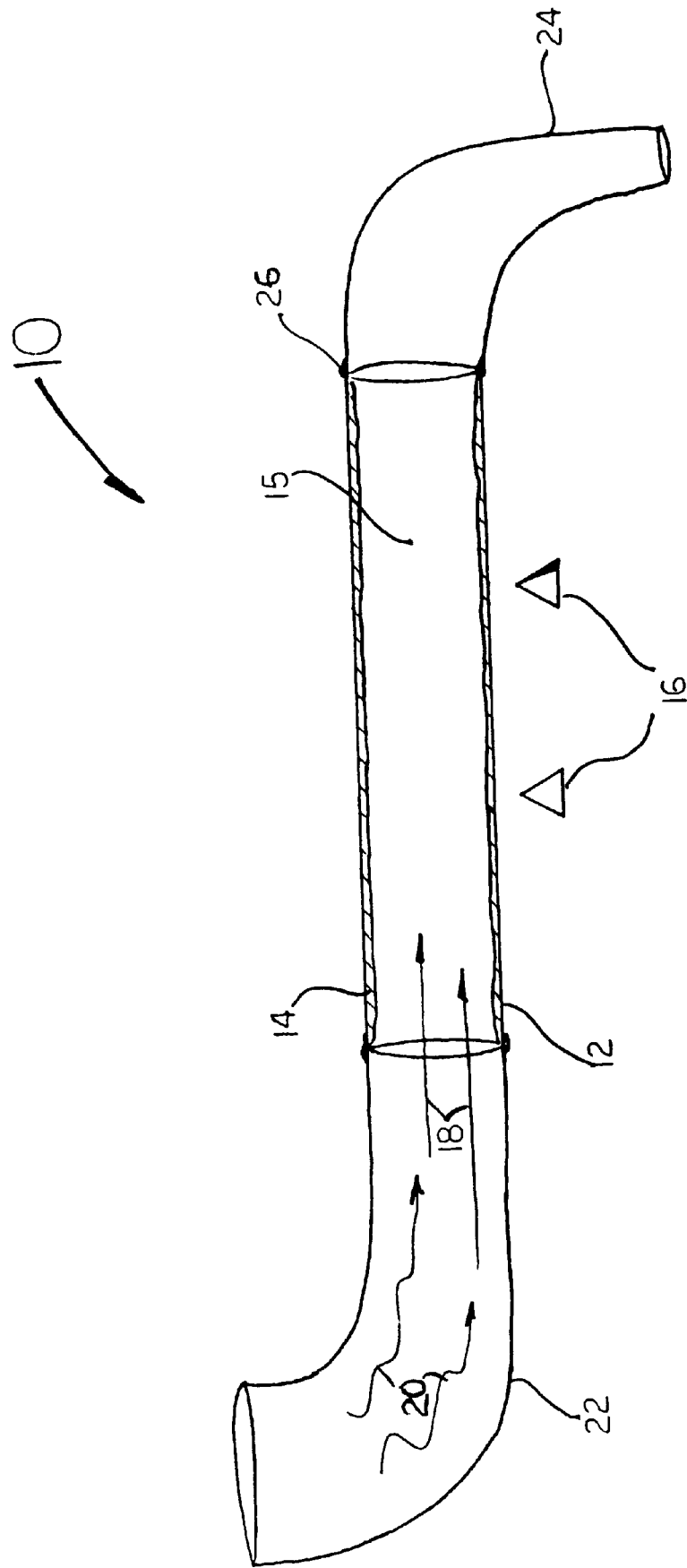

METHOD OF DEHALOGENATION USING DIAMONDS

CONTRACTUAL ORIGIN OF THE INVENTION

The United States Government has rights in this invention pursuant to the employer-employee relationship of the U.S. Department of Energy and the inventor.

BACKGROUND OF THE INVENTION

1. Field of the Invention

This invention relates to a method for producing olefins and halogenated olefins, and more specifically, this invention relates to a method for using diamonds and carbon composite materials containing diamonds to catalyze elimination reactions of halogenated compounds to produce olefins and halogenated olefins.

2. Background of the Invention

Dehalogenation reactions and hydrodehalogenation reactions are combined to produce polyvinyl chloride. Current production capacity for polyvinyl chloride is approximately 9.8 billion pounds annually.

The above-mentioned elimination reaction is typically performed thermally at temperatures ranging from 500° C. and 600° C. However, the use of activated carbons in the reaction mixture has resulted in lowering the temperature requirements to between 300° C. and 400° C. Catalytic cracking on pumice or charcoal impregnated with $BaCl_2$ or $ZnCl_2$ also has been utilized. However, these procedures have not been widely adopted due to the limited life of the resulting catalysts.

Other efforts for enhancing the catalytic activity of activated carbon in these reactions include incorporating nitrogen materials into the lattice structure of the carbon. While the industrial applicability of the resulting carbon material is not known, it is likely that the resulting carbon is more expensive than typical activated carbon materials.

A need exists in the art for a method to produce olefins and monohalogenated olefins from dihalogenated aliphatic compounds via elimination reactions that can be performed at temperatures much lower than those required in thermal processes. The method should be economical and also employ a reusable catalyst which does not require any preparation.

SUMMARY OF THE INVENTION

It is an object of the invention to provide a method for dehalogenating and hydrodehalogenating halogenated compounds that overcomes many of the disadvantages of the prior art.

Another object of the present invention is to provide a method for converting alkyl halides to olefins and halogenated olefins. A feature of the invention is the use of diamonds as a catalyst for the elimination reaction. An advantage of the invention is that the reaction can proceed at temperatures much lower than those required for thermal reactions.

Still, another object of the present invention is to provide an economical method for producing vinyl chloride. A feature of the invention is the dehalogenation and hydrodehalogenation of 1,2 allyl halide using diamond catalysts. An advantage of the invention is that the diamond catalyst can be utilized for elimination reactions at temperatures of between 200° C. and 350° C., and preferably between 250° C. and 290° C. as compared to 500° C. to 600° C. currently used in thermal processes.

Briefly, the invention provides for a method for preparing olefins and monohalogenated olefins comprising contacting halogenated compounds with diamonds for a sufficient time and at a sufficient temperature to convert the halogenated compounds to olefins.

Also, provided is a device for producing olefins from halogenated compounds comprising an underlayment defining a chamber; a diamond coating on a surface of the underlayment; means for hermetically sealing the underlayment to an ingress manifold and an egress manifold so as to facilitate fluid flow through the chamber; and means for heating the chamber.

A method for producing vinyl chloride is also provided comprising contacting 1,2 dichloroethane with a diamond catalyst for a sufficient time and at a sufficient temperature to convert the 1,2 dichloroethane to a product in a hydrodechlorination reaction.

BRIEF DESCRIPTION OF THE DRAWING

The invention together with the above and other objects and advantages will be best understood from the following detailed description of the preferred embodiment of the invention shown in the accompanying drawing, wherein:

FIG. 1 is a schematic diagram of a device for converting halogenated compounds in an elimination reaction; in accordance with features of the present invention.

DETAILED DESCRIPTION OF THE INVENTION

Generally, the invention provides for a method for economically converting halogenated compounds to olefins and halogenated olefins. Surprisingly and unexpectedly, the inventors found that contrary to the generally held belief, diamonds which contain $sp^3$ (saturated) carbons are catalytically active. Furthermore, the inventors have determined that these diamonds are the most reactive carbon-material catalysts for elimination reactions such as dehalogenation of halogen-alkanes and dehalogenation of 1,2 dihalogen-saturated compounds.

While the following examples provide conversion data for specific halogenated reactants, this is not to be construed as the method being relegated to conversion of just those compounds. In fact, any halogenated alkanes, including alpha-beta dihalogen-saturated compounds, are conversion candidates. Specifically, conversion candidates include, but are not limited to, 1,2 dichloroethane, 1,2 difluoroethane, 1,2 dichlorocylcohexane, 1-chlorohexadecane, 1-flourononane, and combinations thereof. Alkyl halogenated aromatics (i.e., aromatic compounds with halogenated substitutions on the alkyl moiety) are also suitable conversion candidates using the invented method. Any halogenated alkyl aromatic is a suitable feedstock. Exemplary aromatics for conversion include, but are not limited to chloro-ethyl benzene, fluoroalkyl benzene, and 1,2 dichloro-1-phenyl ethane.

In the case of dehalogenation of alpha-beta dihalogen aliphatic compounds, various diamonds catalyze two different reactions at different extents and selectivities. In one reaction, hydrodehalogenation is effected with the elimination of HCl and the formation of chlorine-containing olefins. In the other reaction, dehalogenation, chlorine gas is eliminated and neat olefins are produced.

The invented elimination method, and a device embodying the invented elimination process, is depicted in numeral 10 in FIG. 1.

Generally, the device 10 employs an underlying substrate 12 onto which a fixed bed of diamonds 14 positioned. The diamond bed or coating serves to define a reaction chamber 15 in which the elimination reactions occur.

The underlayment or substrate 12 is configured so as to maintain a controlled reaction atmosphere in the chamber 15, in that ambient air or fluids are excluded from the confines of the chamber formed by the underlying substrate. In one embodiment, the underlayment 12 mimics the inside surface of a tube or conduit with diamond or carbon catalyst material coating the surface. The tubular reaction chamber is adapted to be attached to a feed gas manifold 22 and a product egress manifold 24. Any weldments 26 or other manifold attachment means which remain intact at temperatures up to 400° C. are suitable. Generally, the attachment between the substrate and manifolds 22, 24 are such so as to isolate the feed gas and product gas from ambient environment. Hermetic seals can serve as suitable attachment means 26, particularly when gaseous reactants and product are involved.

In operation, the reaction chamber 15 receives reactant fluid 18 such as 1,2 dihalogenated compounds. Viscosity of the reactant fluid, at the reaction temperature, will determine if the feed is neat or aided by carrier fluid 20, such as an inert carrier gas (e.g., nitrogen, argon, helium).

Viscosity of the reactant fluid 18 is adjusted so as to maximize exposure of the fluid to the diamond bed. Maximum exposure is typically effected when the reactant/diamond weight percent ratios, discussed infra, are utilized. Higher reaction temperatures will obviate the need for protracted residence times. Required temperatures are provided either via external heat application 16, or by preheating the fluid 18 and/or carrier gas 20 upstream from the reaction chamber.

Aside from a tubular fixed bed diamond catalyst bed described above, other configurations also can be utilized, as can fluidized bed designs.

Diamond Detail

Several types of diamonds, both natural and synthetic, are utilized as catalysts in the invented method. The majority of the diamonds have a cubic crystalline structure.

Mono-crystalline and polycrystalline diamonds are suitable catalytic candidates. Exemplary mono-crystalline cubic diamonds include many natural diamonds, such as those available from Kay Industrial Diamond Corporation of Florida.

Nanosize diamonds are produced by several methods. For example, nanosize diamonds are the detonation products of reactions described throughout the scientific literature, including "Diamonds in Detonation Soot," *Nature* Vol. 333, pp 440 (Jun. 2, 1988), incorporated herein by reference. Additional methods for producing and modifying nanosized diamonds are disclosed in "Influence of the Molecular Structure of Explosives on the Rate of Formation, Yield, and Properties of Ultradisperse Diamond," *Combustion, Explosion, and Shock Waves*, Vol. 30, No. 2, pp 235–238 (Plenum Publishing Corp., New York, N.Y. 1994), which is a translation of Fizika Goreniya i Vzryva, Vol. 30, No. 2, pp. 102–106, March–April 1994, also incorporated herein by reference. Nanosize diamonds of from 2–20 nanometers are produced in methods described in "Synthesis of Ultradispersed Diamond in Detonation Waves" *Combustion, Explosion, and Shock Waves*, Vol. 25, No. 3, pp 372–379, (Plenum Publishing Corp., New York, N.Y. 1994), which is a translation of Fizika Goreniya i Vzryva, Vol. 25, No. 3, pp 117–126, May–June, 1989, incorporated herein by reference.

Other sources and methods for obtaining nanosized diamonds can be found in U.S. Pat. No. 5,709,577, issued on Jan. 20, 1998, and incorporated herein by reference.

The inventors have found that synthetic nanosize, monocrystalline diamonds have a very high activity and selectivity for hydrodehalogenation of 1,2 halogenated aliphatic compounds versus dehalogenation reactions. Furthermore, it was determined that selectivity for the hydrodehalogenation reaction is improved by low temperature and shorter reaction time. As such, the enhanced hydrodehalogenation catalysis provided by nanosized diamonds makes this catalyst particularly attractive for low-cost production of vinyl chloride monomer.

Suitable nanosize diamonds for use in the invented method have particles with a diameter of from about 5 to 500 nm and preferably from about 10 to about 100 nm. Exemplary polycrystalline diamonds include several industrial diamonds, such as the Mypolex products available from DuPont®, and some very rare natural diamonds (known as carbonado).

Table 1 below lists the various diamond types utilized as catalysts in the present method.

TABLE 1

Diamond-based catalysts

| Material | Crystalline Structure | Particle Size |
|---|---|---|
| Natural Diamond | cubic, monocrystalline | 0.1 µm |
| Mypolex | polycrystalline | 0.1 µm |
| Nanosize carbon composite ($sp^3 + sp^2$) | cubic and hexagonal | <0.02 µm |
| Nanosize diamonds | cubic, monocrystalline | <0.02 µm |

The catalytic activity of the diamonds was compared with that of other carbon materials, namely graphite (at 99+% purity, available through Alpha AESAR, Ward Hill, Mass.) having a surface area of 7 m$^2$/g; Carbon Black BP2000 (available through Cabot Corp., Boston, Mass.) having a surface area of 1475 m$^2$/g; and silicone carbide (99.8% pure, Alpha) at −325 mesh. The results of this comparison are depicted in Examples 8 through 10, discussed infra.

Elimination Detail

The following bench-top, experimental protocol is provided merely to illustrate the feasibility of the invented method. As such, the invented method is not relegated to such micro test scales but rather as a prototype for industrial scale processes, as embodied in the schematic illustration of FIG. 1.

In all laboratory-scaled experiments, reactions were performed in sealed Pyrex tubes. Typically, approximately 2 to 100 times more reaction substrate by weight is used than diamond catalyst material. Preferable weight ratios of substrate to diamond (Substrate weight: diamond catalyst weight) are from 2.5:1 to 10:1. As such, the bench-top processes utilized 25 mg to 50 mg of substrate, and 2.5 to 20 mg of catalyst.

Temperatures are selected so that no conversion, or less than 3 percent conversion, occurs without catalysts. As such, temperatures were selected from between 200° C. and 350° C.

General Elimination Reaction

Generally, the elimination reaction of monohalogenated compounds proceeds by the following reaction:

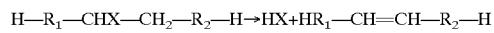

Where:

$R_1$ and $R_2$ are saturated aliphatic moieties (both linear aliphatic and saturated rings) having from 0 to 30 atoms of carbon or aromatic moieties (e.g., benzene, naphthalene, etc.); and X is a halogen (fluorine, chlorine, bromine, or iodine).

The following elimination reaction removes adjacent or alpha-beta halogens from the dihalogenated organic compounds. Either of the two following elimination reactions may take place, with various selectivities:

a: hydrodehalogenation:

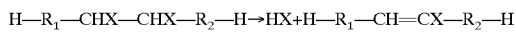

b: dehalogenation:

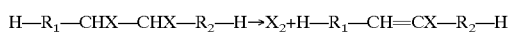

$R_1$, $R_2$, and X are the same as above.

Although the halogen may be chlorine, fluorine, bromide or iodine, chlorine and bromine are the preferred halogens for use with the present process.

Reaction Detail for 1,2 Dihalogen Conversion

Trans-1,2 dichlorocyclohexane was used as a model compound for measuring diamond catalytic activity in some dehalogenation and hydrodehalogenation reactions.

In the dehalogenation of 1,2,dichlorocyclohexane to cyclohexene (Equation 1) and the hydrodehalogenation to chlorocyclohexene (Equation 2), the following reactions take place simultaneously:

Equation 1

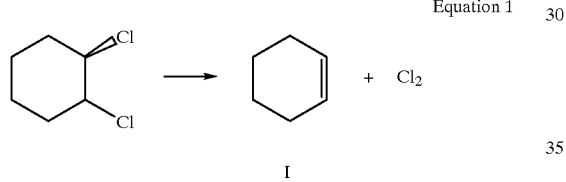

I

Equation 2

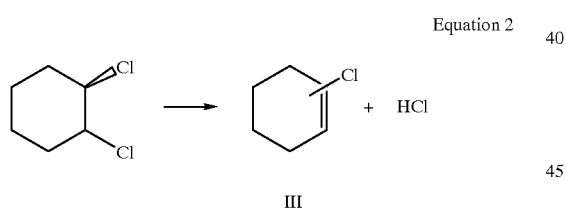

III

Small amounts of the HCl formed in the hydrodehalogenation reaction (Equation 2) may react with cyclohexene formed in Equation 1 to form chlorocyclohexane (III) in a secondary reaction process depicted in Equation 3.

Equation 3

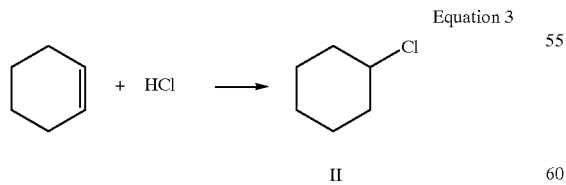

II

Some of the chlorocyclohexenes (III) formed via hydrodehalogenation (Equation 2) further eliminate HCl and aromatize to benzene (V). Small amounts of cyclohexadiene (IV) and of phenyl-cyclohexane (VI) also were observed in some cases.

Reaction Detail for Halogen-alkane Conversion

Chlorohexadecane (VII) was used as a model compound for hydrodechlorination conversion reactions and F-nonane (VIII) for hydrodefluorination reactions. Representative reaction sequences are Equations 4 and 5 below:

Equation 4

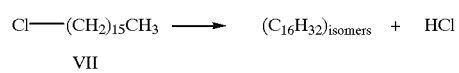

VII

Equation 5

VIII

Examples 1 through 12 reports experimental data as follows:

1. For trans-1,2 dichlorocyclohexane (Examples 1–8):
    a.) Percent (mole percent) conversion of trans-1,2 dichlorocyclohexane to products;
    b.) Percent selectivity of various products;
    c.) Selectivity of aromatization of chloro-cyclohexenes to benzene:
        moles benzene/(moles benzene+moles chlorocyclohexenes)
    d.) Selectivity of hydrodehalogenation reaction versus dehalogenation reaction calculated by the following expression:
        (chloro-cyclohexenes+cyclohexadiene+benzene)/(cyclohexene+Cl-cyclohexane);
        in which all quantities are expressed in moles.

2. For 1-fluorononane and 1-chlorohexadecane conversions (Examples 9–12):
    a.) Percent (mole %) conversion of the initial halogenated paraffins to isomers of olefin with the same carbon number.

Various products and intermediates were obtained with the conversion reactions. These products and intermediates are designated in the Examples as follows:

| Product/Intermediate Number | Generic Description |
|---|---|
| I | Cyclohexene |
| II | Cl-cyclohexane |
| III | Isomers of Cl-cyclohexene |
| IV | Cyclohexadiene |
| V | Benzene |
| VI | Phenyl-cyclohexane |

EXAMPLE 1

Control

Trans-1,2 dichlorocyclohexane was heated in a sealed Pyrex tube for one hour at 290° C. No reaction was observed.

EXAMPLE 2

Trans-1,2 dichlorocyclohexane was heated for one hour at 290° C. in the presence of 40 weight percent natural diamonds. The following conversions and selectivities for both products and reactants were obtained.

| | | PRODUCTS | | | | | |
|---|---|---|---|---|---|---|---|
| Time | Conversion | Selectivity Percents | | | | | |
| (min) | (%) | I | II | III | IV | V | VI |
| 60 | 56 | 10 | 39 | 10 | 2 | 27 | 12 |

| | | REACTANTS | |
|---|---|---|---|
| Time | Conversion | Selectivity Percents | |
| (min) | (%) | V/(III + V), % | HCl removal/Cl$_2$ Removal |
| 60 | 56 | 72 | 0.8 |

EXAMPLE 3

Trans-1,2 dichlorocyclohexane was heated for one hour at 280° C. in the presence of 10 weight percent Mypolex. The following conversion and selectivities were obtained:

| | | PRODUCTS | | | | | |
|---|---|---|---|---|---|---|---|
| Time | Conversion | Selectivity Percents | | | | | |
| (min) | (%) | I | II | III | IV | V | VI |
| 60 | 32 | 38 | 37 | 10 | 0 | 11 | 4 |
| | 31 | 36 | 37 | 10 | 0 | 14 | 3 |

| | | REACTANTS | |
|---|---|---|---|
| Time | Conversion | Selectivity Percents | |
| (min) | (%) | V/(III + V), % | HCl removal/Cl$_2$ Removal |
| 60 | 32 | 53 | 0.3 |
| | 31 | 58 | 0.3 |

Example 3 illustrates the catalytic activity and selectivity of Mypolex and also the reproducibility of the micro tests.

EXAMPLE 4

Trans-1,2 dichlorocyclohexane was heated at 280° C. for 20, 40, and 60 minutes in three separate tests, in the presence of 10 weight percent nanosize carbon composite. These tests prove that the relative ratio of the hydrodehalogenation versus dehalogenation does not change with time for the above-mentioned catalyst.

| | | PRODUCTS | | | | | |
|---|---|---|---|---|---|---|---|
| Time | Conversion | Selectivity Percents | | | | | |
| (min) | (%) | I | II | III | IV | V | VI |
| 20 | 41 | 26 | 32 | 14 | 3 | 20 | 5 |
| 40 | 47 | 29 | 32 | 12 | 2 | 21 | 4 |
| 60 | 77 | 29 | 37 | 9 | 0 | 19 | 6 |

| | | REACTANTS | |
|---|---|---|---|
| Time | Conversion | Selectivity Percents | |
| (min) | (%) | V/(III + V), % | HCl removal/Cl$_2$ Removal |
| 20 | 41 | 58 | 0.6 |
| 40 | 47 | 63 | 0.6 |
| 60 | 77 | 42 | 0.6 |

EXAMPLE 5

Trans-1,2 dichlorocyclohexane was heated for 20 minutes at 280° C. and in a separate experiment for 20 minutes at 290° C. In each case, the reaction was performed in the presence of 10 weight percent nanosize carbon composite.

| | | PRODUCTS | | | | | |
|---|---|---|---|---|---|---|---|
| Time | Conversion | Selectivity Percents | | | | | |
| (min) | (%) | I | II | III | IV | V | VI |
| 280 | 38 | 32 | 22 | 16 | 4 | 21 | 5 |
| 290 | 56 | 21 | 36 | 15 | 0 | 20 | 8 |

| | | REACTANTS | |
|---|---|---|---|
| Temp | Conversion | Selectivity Percents | |
| (° C.) | (%) | V/(III + V), % | HCl removal/Cl$_2$ Removal |
| 280 | 38 | 57 | 0.6 |
| 290 | 56 | 56 | 0.6 |

EXAMPLE 6

Trans-1,2 dichlorocyclohexane was heated at 280° C. for 20, 40, and 60 minutes in three separate tests, in the presence of 10 weight percent monocrystalline cubic nanosize diamonds.

| | | PRODUCTS | | | | | |
|---|---|---|---|---|---|---|---|
| Time | Conversion | Selectivity Percents | | | | | |
| (min) | (%) | I | II | III | IV | V | VI |
| 20 | 23 | 12 | 3 | 59 | 4 | 20 | 2 |
| 40 | 31 | 14 | 4 | 58 | 4 | 17 | 3 |
| 60 | 53 | 12 | 6 | 59 | 5 | 13 | 6 |

| | | REACTANTS | |
|---|---|---|---|
| Time | Conversion | Selectivity Percents | |
| (min) | (%) | V/(III + V), % | HCl removal/Cl$_2$ Removal |
| 20 | 23 | 25 | 5.3 |
| 40 | 31 | 23 | 4.5 |
| 60 | 53 | 18 | 4.3 |

EXAMPLE 7

In three separate experiments, trans-1,2 dichlorocyclohexane was heated for one hour at 270° C., 280° C. and 290° C., each in the presence of 10 weight percent nanosize diamonds. The data indicate a decrease in the selectivity toward hydrodechlorination with an increase in reaction temperature.

| | PRODUCTS | | | | | | |
|---|---|---|---|---|---|---|---|
| Time | Conversion | Selectivity Percents | | | | | |
| (min) | (%) | I | II | III | IV | V | VI |
| 270 | 7 | 9 | 7 | 28 | 0 | 44 | 12 |
| 280 | 53 | 12 | 6 | 59 | 5 | 13 | 6 |
| 290 | 76 | 5 | 16 | 50 | 2 | 14 | 13 |

| | REACTANTS | | |
|---|---|---|---|
| Temp | Conversion | Selectivity Percents | |
| (° C.) | (%) | V/(III + V), % | HCl removal/Cl$_2$ Removal |
| 270 | 7 | 61 | 4.6/5.6 |
| 280 | 53 | 18 | 4.3/5.3 |
| 290 | 76 | 22 | 3.1 |

EXAMPLE 8

The catalytic reactivity and selectivity of various forms of diamond discussed supra were compared with other products. Trans-1,2-dichlorocyclohexane was reacted for one hour at 290° C. in the presence of various types of diamond materials, graphite, carbon black BP 2000, and silicon carbide. The following results were obtained.

| Catalyst | Conversion, % | HCl removal/Cl$_2$ removal |
|---|---|---|
| 40 wt. % Natural Diamond | 56 | 0.8 |
| 10 wt. %* Mypolex (0.1 μm) | 32 | 0.3 |
| 10 wt. % nanosize carbon composite | 82 | 0.4 |
| 10 wt. % nanosize diamond | 76 | 3.1 |
| 50 wt. % graphite | 36 | 0.2 |
| 10 wt. %** Carbon black BP 2000 | 6 | 3.8 |
| 50 wt. % Silicon carbide | 13 | 1.3 |

*This data was obtained at 280° C. Massive carbon formation is observed at higher temperatures.
**For reactions which were performed at 310° C., conversion was 14% and the selectivity HCl removal/Cl$_2$ removal was 1.7.

The data in Examples 6, 7, and 8 show that nanosize diamonds have a very high activity and selectivity for hydrodehalogenation and that their selectivity for this reaction is further improved by low temperature and shorter reaction times. In fact, this example shows all selectivities greater than 4.0. Other examples provide selectivities less than one.

EXAMPLE 9

1-fluorononane was heated for one hour at various temperatures in the range of 200–310° C. in the presence of various carbon materials. The conversion to isononenes was as follows:

| | Conversion at ° C., % | | | | | |
|---|---|---|---|---|---|---|
| Catalyst | 220 | 230 | 240 | 250 | 300 | 310 |
| None | — | — | — | — | 1 | — |
| Natural Diamond | 44 | 91 | 96 | — | 100 | — |
| Mypolex | 0 | 3 | 63 | 95 | 100 | — |
| Nanosize Carbon Composite | — | — | — | 1 | 3 | 100 |
| Nanosize Diamonds | 2 | 100 | — | 100 | — | — |
| Graphite* | | 4 | 7 | 23 | 29 | — |
| Carbon Black BP 2000 | | 1 | 1 | 91 | 97 | — |
| Silicon Carbide* | — | <2 | — | — | — | |

*Due to the low surface area, graphite and silicon carbide were used as 50 weight percent of fluorononane.

EXAMPLE 10

In two separate experiments, 1-chlorohexane and 1-chlorohexadecane were heated for one hour at 300° C. in the presence of 10 weight percent of various catalysts. The conversions to iso-hexenes and iso-hexadecenes were as follows:

| | Conversion % | |
|---|---|---|
| Catalyst | 1-Cl-nC$_6$H$_{13}$ | 1-Cl-nC$_{16}$H$_{33}$ |
| None | 0 | 0 |
| Natural Diamond | 8 | 7 |
| Mypolex | 18 | 33 |
| Nanosize Carbon Composite | 57 | 50 (average) |
| Nanosize Diamonds | 29 | — |
| Graphite* | 3 | 10 |
| Carbon Black BP 2000 | 1 | 3 |
| Silicon Carbide* | | 5 |

*Due to low surface area, graphite and silicon carbide were used as 50 weight percent of chloro-hydrocarbons.

EXAMPLE 11

To assess the competitive reactivity of 1-fluorononane and 1-chlorohexadecane in the presence of a diamond catalyst, a 1:1 by weight mixture of the two compounds was heated for one hour at 300° C. in the presence of 10 weight percent of Mypolex (0.1 micron. The conversion of the two compounds was calculated as a percent of each initial quantity. This example illustrates unexpectedly higher catalytic activity of diamond for dihydrofluorination versus dihydrochlorination reactions.

| Compound | Conversion, % |
|---|---|
| 1-fluorononane | 90 |
| 1-chlorohexadecane | 29 |

EXAMPLE 12

To assess the thermal reactivities of 1-flurononane and 1 chlorohexadecane and the thermal interaction between 1-fluorononane and 1-chlorohexadecane, several thermal runs were performed at 390° C. for one hour.

| 1-F-nC$_9$H$_{19}$/1-Cl-nC$_{16}$H$_{33}$ | Reaction: Conversion, % | |
| --- | --- | --- |
| molar ratio | 1-F-nC$_9$H$_{19}$ | 1-Cl-nC$_{16}$H$_{33}$ |
| 1:0 | 0 | |
| 0:1 | | 46 (average)* |
| 1:0.87 | 75 | 71 |
| 1:0.03 | 4 | 11 |

*some cracking observed.

Nonenes (C9-olefins) were a major product of the hydrodefluorination reaction of 1-fluorononane in Example 12. It is important to note that even at 390° C. in the absence of diamond, no dehydrofluorination takes place thermally. Hydrofluorination takes place only in binary mixtures of alkyl fluorides and alkyl chlorides. Small amounts of 1-chlorononane was also formed, probably from the addition of HCl (which was formed from hydrodechlorination of Cl-hexadecane) to the nonenes.

While the invention has been described with reference to details of the illustrated embodiment, these details are not intended to limit the scope of the invention as defined in the appended claims.

The embodiment of the invention in which an exclusive property or privilege is claimed is defined as follows.

We claim:

1. A method for preparing olefins and halogenated olefins comprising:

contacting halogenated compounds with diamonds for a sufficient time and at a sufficient temperature to convert the halogenated compounds to olefins and halogenated olefins.

2. The method as recited in claim 1 wherein the temperature is selected from between 200° C. and 350° C.

3. The method as recited in claim 1 wherein the temperature is selected from between 220° C. and 290° C.

4. The method as recited in claim 1 wherein the halogenated compound is present with the diamond in a weight ratio of between 10:1 and 20:1.

5. The method as recited in claim 1 wherein the diamond is of a species having a cubic monocrystalline structure.

6. The method as recited in claim 5 wherein the species is a natural diamond, or nanosize diamond composite, or nanosize diamond, or combinations thereof.

7. The method as recited in claim 1, wherein the halogenated hydrocarbons undergo an elimination reaction.

8. The method as recited in claim 1 wherein the diamond is monocrystalline cubic nanosize diamond and the halogenated compounds are halogenated saturated compounds which are converted preferentially via hydrodehalogenation.

9. The method as recited in claim 8 wherein the halogenated compounds are converted via hydrodehalogenation with at least 80 percent selectivity.

10. The method as recited in claim 1 wherein the halogenated hydrocarbons are aliphatic compounds selected from the group consisting of 1,2-dichloroethane, 1,2-dichlorocyclohexane, 1-chlorohexadecane, 1-fluorononane, 1,2-difluoroethane, and combinations thereof.

11. The method as recited in claim 1, wherein the halogenated hydrocarbons are alpha-beta dihalogenated aliphatic compounds.

12. The method as recited in claim 1 wherein the halogenated compounds are alkyl chlorinated aromatic compounds.

13. The method as recited in claim 7 wherein the elimination reaction is hydrodehalogenation or dehalogenation.

14. A method for producing vinyl chloride comprising contacting 1,2 dichloroethane with a diamond catalyst for a sufficient time and at a sufficient temperature to convert the 1,2 dichloroethane in a hydrodechlorination reaction.

15. The method as recited in claim 14 wherein the diamond catalyst comprises monocrystalline cubic nanosize diamonds.

16. The method as recited in claim 14 wherein the temperature is between 220° C. and 290° C.

* * * * *